United States Patent [19]
Nobis et al.

[11] Patent Number: 5,137,198
[45] Date of Patent: Aug. 11, 1992

[54] FAST CLOSURE DEVICE FOR LINEAR SURGICAL STAPLING INSTRUMENT

[75] Inventors: Rudolph H. Nobis, Cincinnati; Ronald R. VanOverloop, West Chester; Michael D. Cronin, Cincinnati; Steven W. Hamblin, Loveland, all of Ohio

[73] Assignee: Ethicon, Inc., Somerville, N.J.

[21] Appl. No.: 701,259

[22] Filed: Feb. 16, 1991

[51] Int. Cl.$^5$ .............................................. A61B 17/04
[52] U.S. Cl. ...................................... 227/19; 227/178; 227/179
[58] Field of Search ................. 227/19, 175, 176, 177, 227/178, 179, 180, 181, 182

[56] References Cited

U.S. PATENT DOCUMENTS

| | | | |
|---|---|---|---|
| 3,080,564 | 3/1963 | Strekopitov et al. | 227/19 |
| 3,275,211 | 9/1966 | Hirsch et al. | 227/19 |
| 3,589,589 | 6/1971 | Akopov | 227/19 |
| 4,383,634 | 5/1983 | Green | 227/19 |
| 4,522,327 | 6/1985 | Korthoff et al. | 227/19 |
| 4,527,724 | 7/1985 | Chow et al. | 227/19 |
| 4,869,414 | 9/1989 | Green et al. | 227/19 |

FOREIGN PATENT DOCUMENTS

8302247 7/1983 PCT Int'l Appl. .................. 227/176

*Primary Examiner*—Frank T. Yost
*Assistant Examiner*—Allan M. Schrock
*Attorney, Agent, or Firm*—Paul A. Coletti

[57] ABSTRACT

A fast closure mechanism for a linear surgical stapling device as described. This comprises a double four-bar linkage which operates to both place a retaining pin into an anvil and properly and quickly approximate the staple cartridge to the anvil. Thereafter, a gap-setting screw is used so that the proper gap is set between the anvil and the cartridge. Firing is accomplished only after the gap is properly set and within the appropriate gap described pre-determined for the instrument. After firing, opening of the stapler may be accomplished with a similar fast opening motion.

18 Claims, 6 Drawing Sheets

FAST CLOSURE DEVICE FOR LINEAR SURGICAL STAPLING INSTRUMENT

FIELD OF THE INVENTION

The invention relates to a disposable linear surgical stapling instrument for forming and implanting at least one rectilinear row of surgical staples in the tissue of a patient, and more particularly to such an instrument having a working gap for use with a single size of surgical staple together with novel safety means which greatly reduce the opportunity for inadvertent or incorrect operation of the instrument. Most specifically, the invention relates to a new fast closure mechanism for such a staple.

BACKGROUND OF THE INVENTION

In recent years there has been an increasing number of surgeons using surgical staples, rather than conventional sutures. This is true because the use of surgical staples and surgical stapling instruments has made many difficult procedures much simpler. Of even more importance, however, is the fact that the use of surgical staples significantly reduces the time required for most procedures, and therefore reduces the length of time for which the patient must be maintained under anesthetic. Many types of surgical stapling instruments have been devised, for many different procedures. The present invention is directed to a linear surgical stapling instrument. This is an instrument which, in a single actuation, implants and forms at least one rectilinear row of surgical staples. Such instruments are used on many different organs and tissues such as the lung, esophagus, the stomach, the duodenum and throughout the intestinal tract.

In its earliest form, the linear surgical stapling instrument was a permanent, multi-use instrument and the surgical staples were manually loaded into the instrument one-by-one. An exemplary surgical stapling instrument of this type is taught in U.S. Pat. No. 3,080,564. While such instruments performed well, they were in general complex in construction, expensive to manufacture, heavy, bulky and difficult both to load with surgical staples and to clean and sterilize after each use.

The next significant improvement in linear surgical stapling instruments was the provision of presterilized, disposable loading units or staple cartridges. U.S. Pat. No. 3,275,211 and U.S. Pat. No. 3,589,589 are exemplary of those relating to permanent, multi-use linear instruments having replaceable staple cartridges. While this improvement significantly reduced the time previously required for hand loading of the staples, the basic instrument still had to be disassembled, cleaned, reassembled and sterilized for each procedure. Such instruments also frequently required maintenance and adjustment.

Even more recently, in view of rising hospital costs, there has been an ever increasing interest in disposable surgical stapling instruments to eliminate as much work as possible (i.e. disassembly, cleaning, reassembly, sterilization and the like) and to be more efficient, while at the same time not having to compromise the surgical procedures. U.S. Pat. No. 4,354,628 and U.S. Pat. No. 4,383,634, for example, each teach a disposable linear surgical stapling instrument. While devices of this sort perform well, since the forwardmost, anvil-carrying jaw is pivoted, the anvil and the cartridge do not approach each other in parallel relationship and only a single gap setting is achievable. In addition, it is sometimes difficult to properly position the tissue to be sutured within the jaws of an instrument of this design. Such instruments are frequently provided in a "tight" suturing version with short legged staples and a "loose" suturing version with staples having longer legs, the surgeon having to select the appropriate instrument for the particular procedure being performed.

The invention described in U.S. Pat. No. 4,527,724 provides a disposable linear surgical stapling instrument which is simple in construction and relatively inexpensive to manufacture. The instrument is characterized by a working gap or range of distances between the anvil and the cartridge over which a single size staple can be properly implanted and formed. The proper and desired setting of the instrument, within the working gap, is easily accomplished through simple manipulation of an adjustment knob at the rear of the instrument with indicator means on each side of the instrument to clearly show when the distance between the anvil and the cartridge is within the working gap. In addition, the gap to which the instrument is set can fall anywhere within the confines of the working gap of the instrument. The gap indicator is additionally designed to show at a glance whether the selected gap falls within the prior art so-called "tight" range or "loose" range.

The instrument of U.S. Pat. No. 4,527,724 is also provided with features normally associated with permanent, multi-use instruments only. The instrument, for example, has an alignment and retaining pin, shiftable to an operative position wherein perfect alignment between the anvil and the staple cartridge is assured, and wherein tissue to be sutured and located between these elements is maintained therebetween. The instrument is provided with a locknut device which precludes rotation of the adjustment knob to secure the desired gap, unless the alignment and retaining pin has been shifted to its operative position. The instrument is also provided with a novel trigger safety which will disable the trigger until the movable jaw of the instrument has been shifted to a position near the working gap. Latch means is also provided for the trigger, to secure the trigger with a snap engagement when the trigger is shifted to its fully actuated position, to give the surgeon a visual tactile and audible indication that the surgical staples have been properly and fully implanted and formed. For purposes of economy and simplicity, much of the instrument is made of appropriate plastic material, while all of the major load-bearing elements of the instrument are metallic. The instrument is so designed that the staple driver is coupled to the trigger at all times.

Nonetheless, the invention of U.S. Pat. No. 4,527,724 is deficient in certain aspects. Primarily, the mechanism used to adjust the staple cartridge from a large opening to a appropriate properly set gap requires manual screwing of a gap setting mechanism. What may be desirable is a fast closure device wherein, with one motion, the gap may be approximated, and then finally set. In addition, it may be desirable to have such an instrument with automatic retaining pin placement and return. In this system, it may further be desirable for the automatic pin placement and return to be coordinated with the closure mechanism such that feedback is given of whether there is an obstruction in front of the retaining pin or in front of the cartridge.

Of course, safety is always an issue and it would be desirable to have a mechanism wherein the firing of the mechanism takes place only within the range of a desirable pre-determined set gap. In some ways, it would be desirable to have a redundant mechanism where the security of safety is incorporated into the mechanism in two ways; first, a typical safety and second, the firing only within the appropriate range of set gap.

SUMMARY OF THE INVENTION

Accordingly, it is an object of the invention for providing a fast closure mechanism within a surgical stapling device preferably a linear surgical stapler.

It is yet another object of the invention to provide an automatic pin placement and return mechanism within the confines of the linear surgical stapler.

It is further an object of the invention to provide such automatic placement in a system which coordinates closure with that of the closure of the cartridge on the anvil section of the stapler.

It is yet another object of the invention to provide a safety mechanism wherein firing of the mechanism takes place only within a pre-determined range of gaps set between cartridge and anvil.

It is finally an object of the invention to provide for such a safety mechanism wherein safety is redundantly provided by a typical safety as well as a gap setting feature.

These and other objects of the invention are disclosed in a linear surgical stapler having a shaft and containing a firing mechanism. A cartridge of staples is provided within the stapler and at the end of the stapler there is an anvil forming surface which forms the staples driven from the firing means into the anvil surface. There is further provided a fast closure mechanism which brings the cartridge into proximal contact with the anvil surface in order to fire the staples using the firing means.

The fast closure mechanism comprises a four-bar linkage incorporated into the stapler body and causing sliding movement of the cartridge along the shaft. Furthermore, the fast closure mechanism is in cooperating relationship with a similar four-bar linkage which operates an automatic pin placement mechanism. The automatic pin placement is done by the second separate four-bar linkage, wherein sliding of the retaining pin is accomplished along the stroke of the slider-crank mechanism operating the staple cartridge. While the automatic pin placement is done via a separate mechanism, the mechanisms are coordinated such that pin placement and cartridge movement occur at roughly the same times. Furthermore, the pin placement mechanism is uniquely formed from a double cam surface such that pin placement and removal occurs readily along this unique four-bar linkage.

Finally, the stapler also contains a gap setting screw which cooperates with the anvil to place the anvil at a desirable distance away from approximately located cartridge. This screw works with an interlocking mechanism such that the firing means is enabled only upon the operation of the screw to place the cartridge within a pre-determined distance from the anvil. When working in cooperation with the typical latch-type safety as disclosed in previous mechanisms, this creates a redundant safety condition so that firing only occurs at a desired safe time.

These and other objects of the invention described herein are more readily understood by an examination of the attached drawings along with a Detailed Description of these Drawings, when taken in conjunction with a Detailed Description of the Invention.

DETAILED DESCRIPTION OF THE DRAWINGS

DETAILED DESCRIPTION OF THE INVENTION

Figure 1:
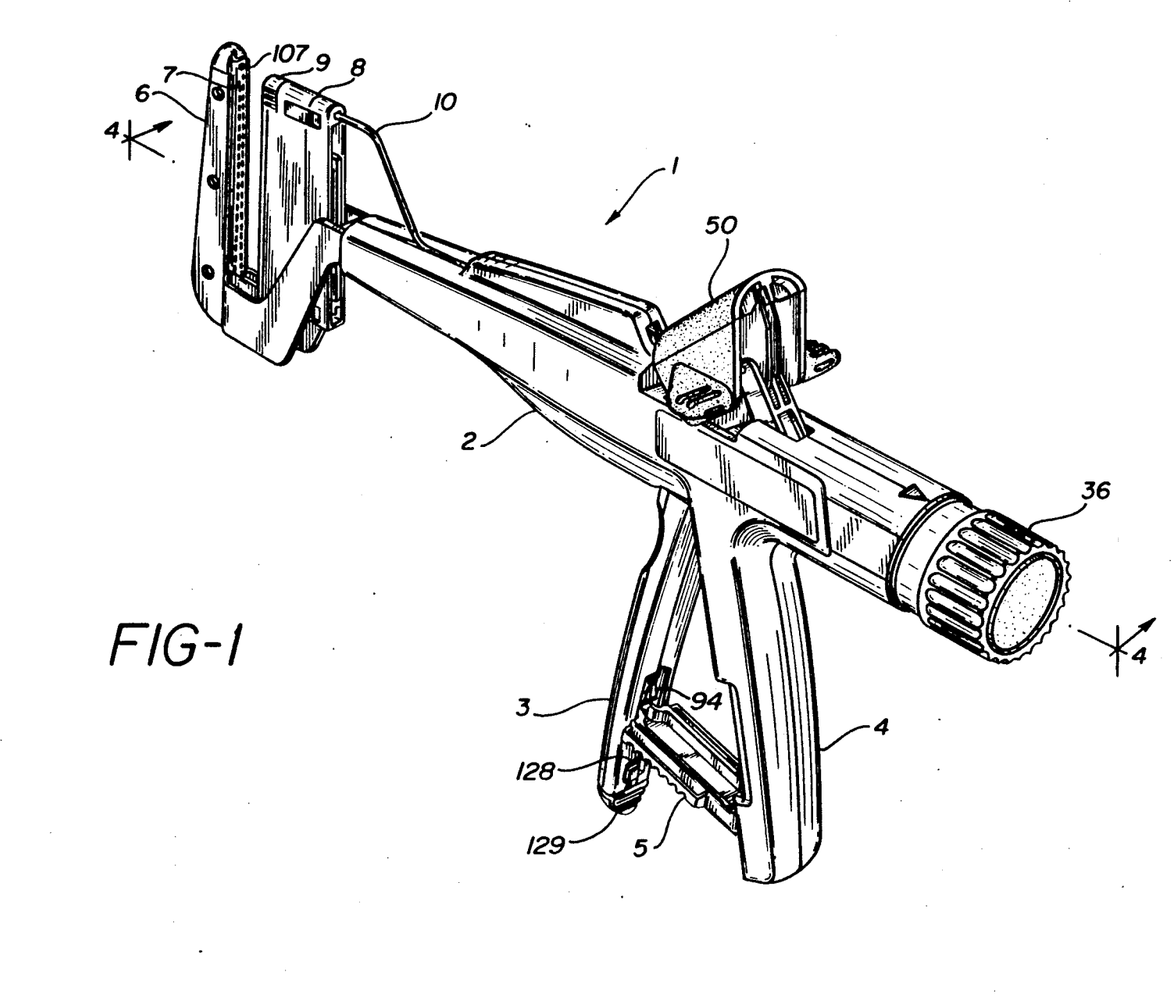
FIG. 1 is a perspective view of a linear surgical stapler containing a fast closure mechanism as described in this invention.
Figure 2:
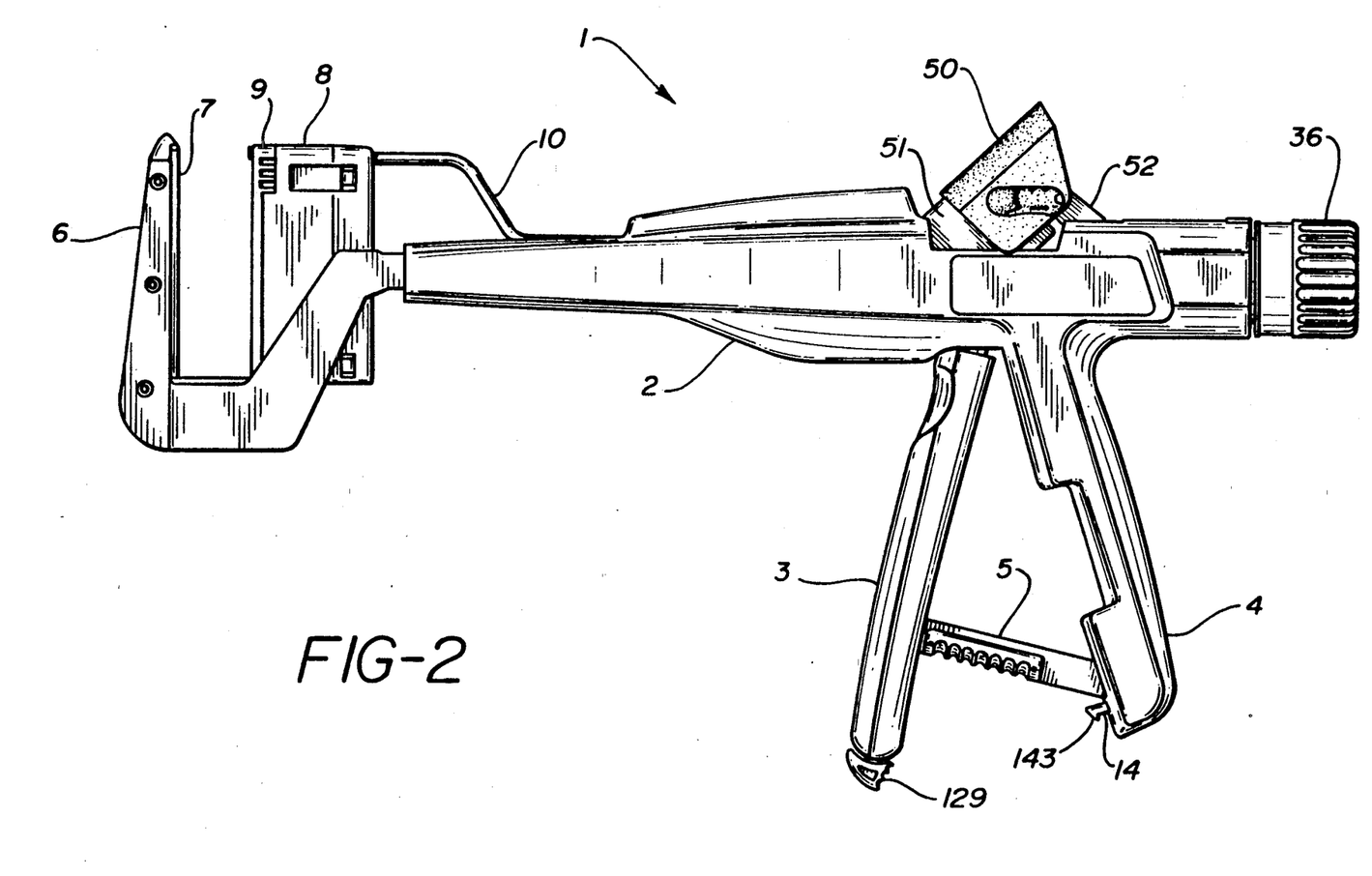
FIG. 2 is a side view of the stapler containing the fast closure mechanism of this invention when the stapler is in its open and locked position.

For convenience and ease of understanding, like parts have been give like index numerals in all of the Figures. Reference is first made to FIGS. 1 and 2. The stapling instrument is generally indicated at 1 and comprises a body 2. The body 2 has a trigger subassembly generally indicated at 3 and a handle subassembly generally indicated at 4. A trigger safety is shown at 5.

At its forward end, the instrument terminates in a fixed jaw generally indicated at 6 supporting an anvil 7. The instrument is also provided with a movable jaw (generally indicated at 8) which comprises, in part, a cartridge 9 for surgical staples. The upper portion of body 2 supports an alignment and retaining pin 10. The alignment and retaining pin 10 extends through movable jaw 8. The pin is shiftable forwardly to a position 107 wherein it also extends into the anvil 7 and fixed jaw 6 to assure that the anvil 7 is properly aligned with the cartridge 9.

Figure 4:
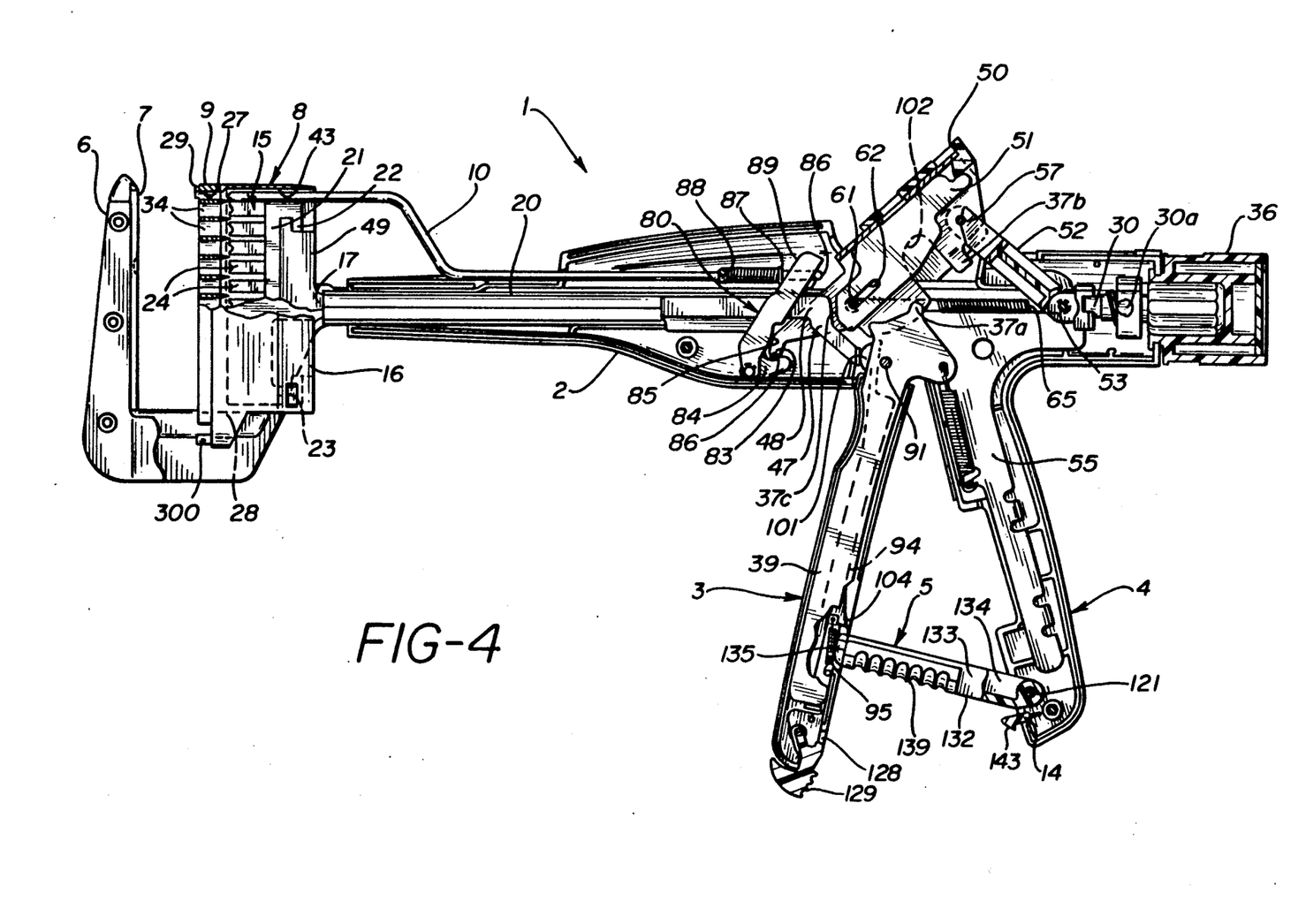
FIG. 4 is a side view of the stapler as seen in FIG. 2 in partial cut-away view.

Reference is now made to FIG. 4, wherein movable jaw 8 and the cartridge/driver subassembly is illustrated in a cross-sectional view. This subassembly comprises the cartridge 9, a staple driver 15, a casing 16, and a driver rod 17. Driver 15, is molded of an appropriate plastic material. Like all of the other plastic parts to be described, driver 15 is formed of a plastic material of adequate strength, suitable for use in a surgical environment, and capable of sterilization by one or more of the known and well accepted methods. Such plastic materials are well known in the art.

The driver 15 is an integral, one-piece element comprising an elongated body 21 having, at its ends, rearwardly extending hook-like elements 22 and 23. The driver 15 is provided with a plurality of forwardly extending tines 24. The tines 24 are equal in number to the number of staples housed in cartridge 9. The forwardly extending tines 24 are arranged in two parallel, spaced rows, with the tines of one row staggered with respect to the tines of the other.

The forward surface of cartridge 9 (i.e., that surface which will face the anvil), is provided with a forwardly extending spacer element 29 adjacent perforation 27 and a forwardly extending spacer 300 adjacent the outermost end of slot 28. These spacers cooperate with the anvil (to be described hereinafter) to determine the forwardmost position of cartridge 9.

The cartridge 9 is provided with a centrally located, longitudinally extending wall, flanked to either side by segmented walls. These walls define two parallel rows of staggered pockets or slots.

Each slot in cartridge 9 is provided at its ends with additional grooves intended to frictionally receive the legs of a surgical staple. Each slot 34 is provided with similar additional grooves so that, in this way, a surgical staple can be loaded in each of slots 34.

As shown in FIG. 4, the tines 24 of driver 15 are insertable within the slots 34 of cartridge 9. It will be noted that the corresponding driver tine 24 overlies the crown of the staple. It will be apparent from this that when the driver 15 is shifted forwardly relative to cartridge 9, the surgical staple will be moved forwardly out of its slot 34. The driver 15 will similarly shove all of the surgical staples from their respective cartridge slots.

The cartridge casing 16 is illustrated in FIG. 4. The casing 16, like driver 15 and cartridge 9, is an integral, one-piece, molded plastic member. It will be noted that driver 15 is shiftably mounted within casing 16.

Figure 6:
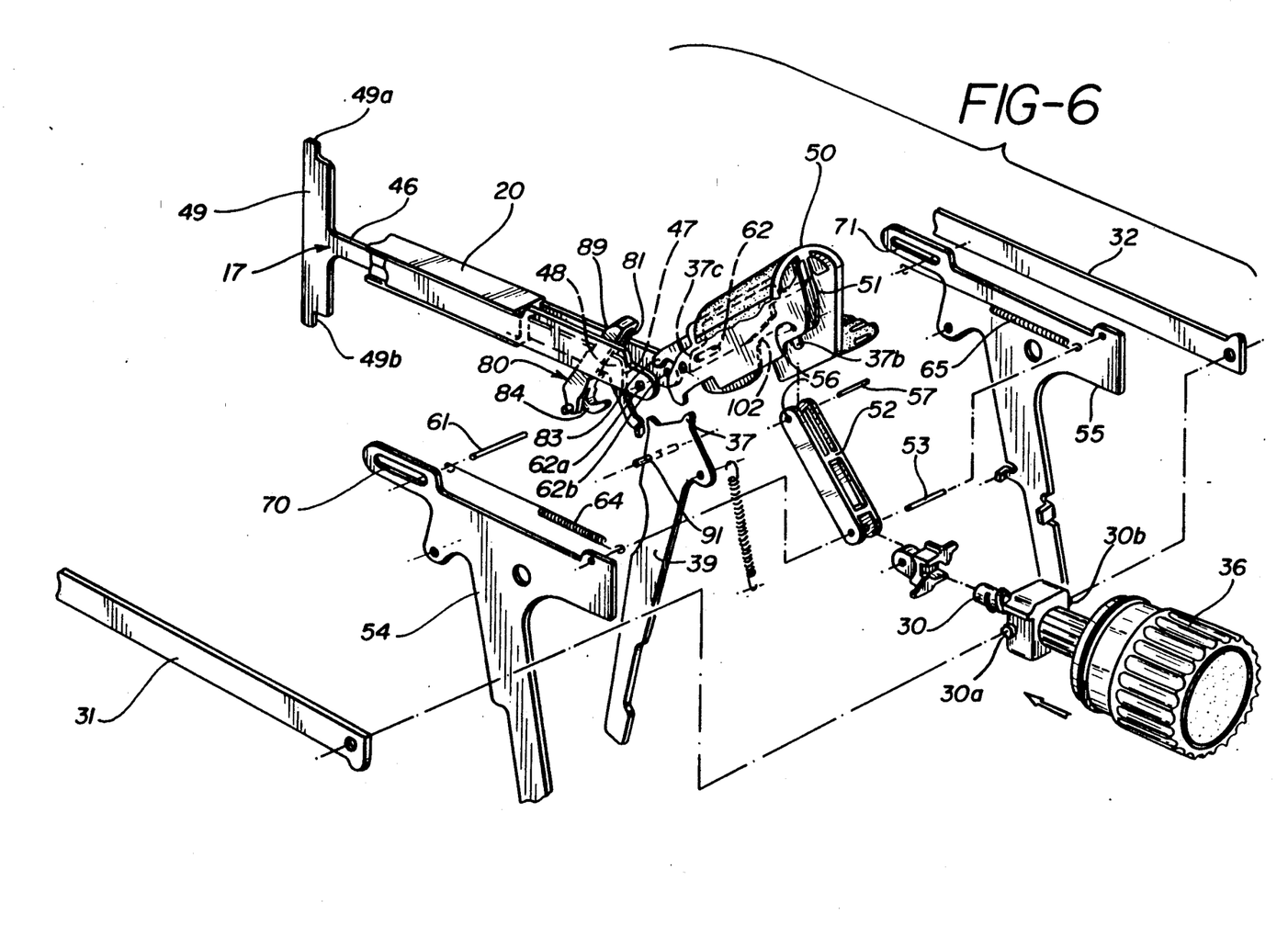
FIG. 6 is a perspective exploded view of various components of the stapler of FIG. 1 containing the fast closure mechanism of this invention.

As also seen in FIG. 6, the driver rod 17 comprises a metallic member having an elongated shank 46. At its rearward end, the elongated shank is bent as at 48 and provided with a transverse contact plate 47. At its forward end, the shank 46 terminates in a plate-like structure 49 having upper and lower lugs 49a and 49b near its forwardmost end. The plate-like forward end 49 of driver rod 17 is located within casing 16 with its lugs 49a and 49b just nicely received within the hook-like portions 23 and 22 respectively, of driver 15. The forwardmost end of the driver rod plate-like structure 49 abuts the elongated body portion 21 of driver 15. Thus, the forward end of the driver rod 17 is locked into engagement with the driver 15 and when the driver rod 17 is shifted in a forward direction, it will shift the driver 15 forwardly as well.

Figure 5:
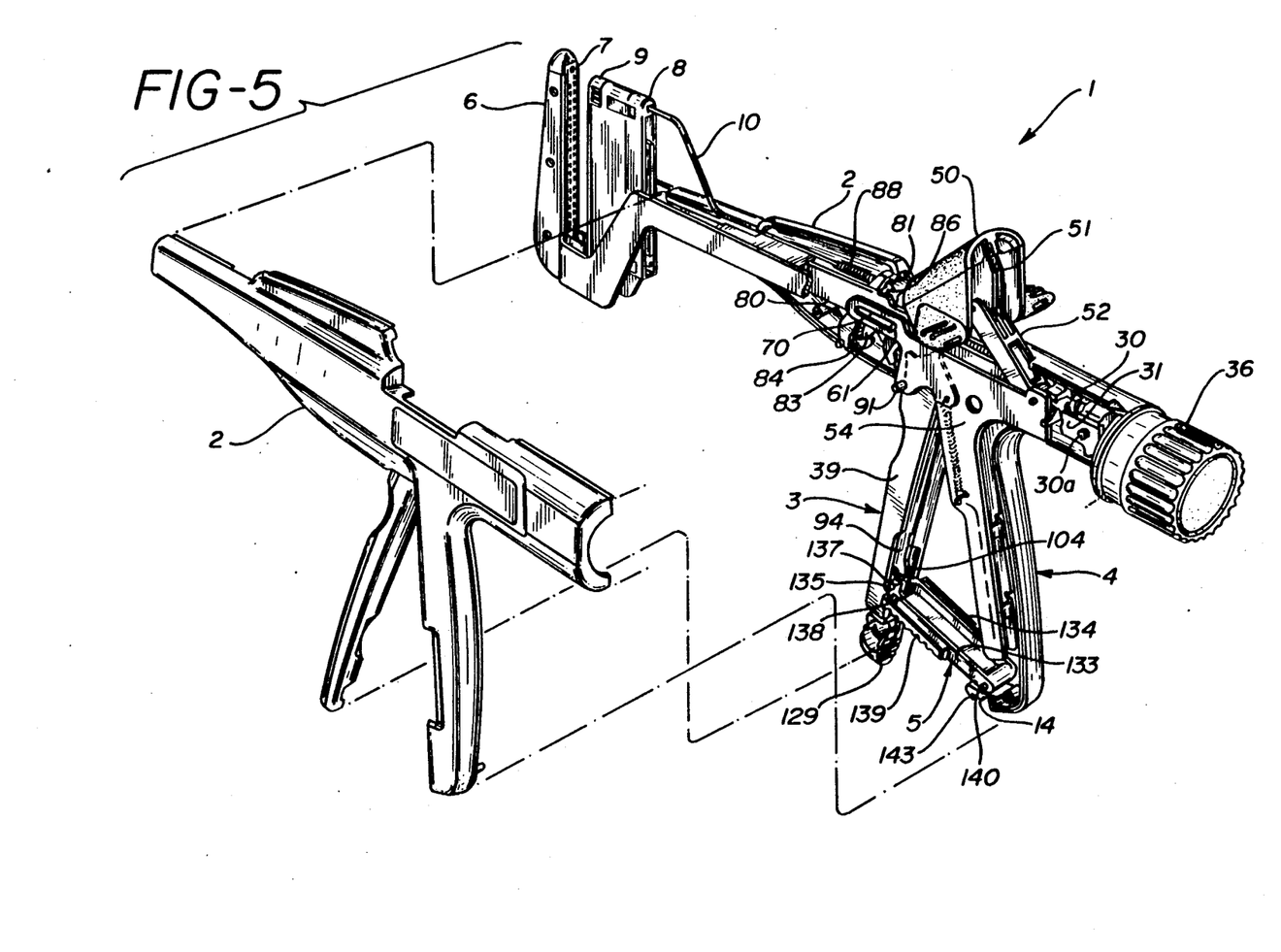
FIG. 5 is a perspective view of the stapler as seen in FIG. 1 with its left half portion removed to reveal some of the inner components of the stapler.

The trigger safety lockout 94 is illustrated in FIGS. 1, 4 and 5. Trigger safety lockout 94 comprises an elongated plastic member having, about midway of its length, an abutment surface 104 to be engaged by trigger safety 5. Adjacent abutment surface 104, the trigger safety lockout 94 is provided with a perforation adapted to receive the upper hood-shaped end of trigger safety lockout spring 95. Near its upper end, the trigger safety lockout 94 has an elongated perforation or slot through which trigger pivot pin 91 extends. Finally, at its uppermost end, the trigger safety lockout 94 is provided with both an upward extension and a locking post, the purpose of which will be described hereinafter.

Trigger safety 5 is a molded plastic member comprising a bottom wall 132, a pair of upstanding side walls 133 and 134 and a front end wall 135. Flanges 137 and 138 extend laterally of side walls 133 and 134. The lower surface of bottom wall 132 and flanges 137 and 138 may contain grooves as at 139 to engage ribs formed in the trigger shroud. The pivot pin 140 is adapted to be received in hole 121 within handle 4. In this way, the trigger safety 5 is pivotally attached to the handle 4. Normally, the trigger safety 5 occupies its extended position illustrated in FIG. 1. In this position, the extension of the trigger safety 5 engages and abuts the abutment surface 104 of trigger safety lockout 94. So long as the trigger safety 5 is in the position shown in FIG. 1, the trigger subassembly 3 cannot be pivoted to its actuated position and is maintained or locked in its unactuated position.

The handle snap lock 14 in FIG. 4 comprises an L-shaped member adapted to fit within the socket in trigger 3. This forward end of the handle snap lock 14 is hook-shaped, as shown at 143. It will be apparent from FIG. 3 that when the trigger assembly 3 is shifted to its fully actuated position adjacent handle assembly 4, the hooked end 143 of handle snap lock 14 will enter the slot 128 in the bottom rear edge of the trigger assembly 3. Once it has entered this slot 128, it will lock the trigger assembly 3 in its fully actuated position, giving the surgeon a visual, audible and tactile indication that the instrument has been fully actuated and the surgical staples have been fully formed and implanted in the tissue being sutured.

In FIG. 1, 2 and 4 the alignment and retaining pin 10 is illustrated in its normal, retracted position. In this position, it will be noted that the forwardmost end of the alignment and retaining pin 10 is located within casing 16, passing through a perforation 43 in the casing 16. Once the tissue to be sutured is located between the fixed jaw 6 and movable jaw 8, the alignment and retaining pin 10 is shoved forwardly by means of the actuating mechanism which will be later described. This causes the forward end of the alignment and retaining pin 10 to pass through the perforation 27 in cartridge 9, and the perforation 107 in anvil 7. In its extended position just described, the alignment and retaining pin 10 accomplishes two purposes. First of all, it assures proper alignment of anvil 7 and cartridge 9 so that the staples will be properly aligned with and clinched by the pairs of anvil pockets when the instrument is actuated. Furthermore, the alignment and retaining pin 10 spans the distance between the fixed jaw 6 and the movable jaw 8 (i.e., between cartridge 9 and anvil 7), assuring that tissue located therebetween will remain therebetween during operation of the instrument.

As can be better seen in FIGS. 3, 4, 5 and 6, there is also disclosed the fast closure mechanism of this invention. In reality, the fast closure mechanism comprises a double cooperating four-bar linkage which will be later described.

The first four-bar linkage is formed in a casing subassembly comprising driver rod or block 20 which is a slider and fitted into the stapler body 2. Casing driver block 20 coordinates with a connecting arm 51 and a crank 52. This crank 52 is also pivotably connected to the stapler body by a pin 53 which is inserted into the two metallic halves of the stapler 54, 55 body. Thus, when force is placed on the connecting arm 51, pin 53 remains stationary. A second pivot 56 on arm 51 and crank 52 causes the connecting arm 51 to crank downward so that both crank 52 and connecting arm 51 rotate to a parallel position on the axis of the stapler shaft 60. This is best seen when analogizing the device 1 as contained in FIGS. 4 and 6 to the motion of arrow A on push lever 50, as in FIG. 3.

When the connecting arm 51 is forced downward, it will be noticed that the third pin 61 contained in the stapler is caused to move forwardly toward the anvil surface. This pin connects hole or slot 62 in connecting arm 51 with the joints 62a, 62b in slider block 20, which contains the cartridge movement mechanism. This is better seen in FIG. 6. This pin 61 slides within the slots, 70 and 71 so that its motion is controlled. This motion is caused to make the slider block subassembly 20 move forward in a rapid fashion. When the slider block subassembly 20 moves forward the pin 61 contained in the connecting arm 51 is made to slide in the slots 70,71 contained in the metallic halves 54,55. It will be noted that a pair of springs 64, 65 hold the third pin 61 to the first pin 53, around which the crank 52 is able to pivot.

In its relaxed state the crank 52 is caused to be in a rearward position, such that the slider block 20 is moved away from anvil 7. Consequently, the cartridge 9 is also removed from anvil 7.

A second, cooperating four-bar linkage is described by the cooperation of connecting arm 51, camming surface 80, and retaining pin 10. The motion of maintaining the retaining pin 10 is constrained along the axis 60 of the shaft body 2 of the stapler 1. It is to be noted that this retaining pin 10 fits into the slot 81 contained in the camming surface 80. The camming surface slot 81 also surrounds the central shaft 48 portion attached to the slider block 20. Thus, while the slider block 20 is able to move independently of the camming surface 80 and the retaining pin 10, the slider block 20 functionally operates so that it must cooperate in at least some fashion with these two different components.

The camming surface 80 cooperates with connecting arm 51 to complete that portion of the four-bar linkage. It can be observed that the final member of the second four-bar linkage is connecting arm 51 connected to the crank 52 and stapler body 2. Therefore, the motion of the connecting arm 51 is quite complex about the stationary stapler body 2. However, for purposes of understanding, it will be sufficient to describe the motion of the connecting arm 51 independent of that of the crank 52 and the stapler body 2, when describing this second four-bar linkage.

Connecting arm 51 has at its forwardmost end a cam 83. When the connecting arm 51 is moved so that the slider block 20 moves forward or rearward on the stapler body, this cam 83 is caused to move in a generally forward or rearward position. It is understood that there is also a slight rotation accomplished by this cam 83.

Motion of cam 83 causes contact with the J-shaped hook 84 of the camming surface 80. If the cam 83 moves forward toward the anvil 7, cam 83 contacts the inner portion 85 of the J-shaped hook 84. If the cam 83 moves rearward it contacts the outer or nub-shaped portion 86 of the camming surface 80.

Motion of the cam 83 against the camming surface 80 causes motion of camming surface 80 toward or away from the anvil 7. This motion of the camming surface 80 causes contact between the extended retaining pin 10 and the camming surface 80 above the casing block subassembly 20, at hook 86 on pin 10 or washer 87 held by spring 88 against outer wall 89 of camming surface 80. It will be noticed that the retaining pin 10 when threaded through slot 81 on the camming surface 80 such that hook 86 is contacted causing the retaining pin 10 to retract, or the washer 87 and spring are contacted, such that retaining pin 10 is caused to move forward toward anvil 7.

In this way, the motion of the fast closure mechanism is actually a complicated cooperating motion between a pair of four-bar linkages. Thus, as in FIG. 3, rotation as indicated at arrow A in a downward position, causes motion forward of the cartridge 9. Furthermore, as a resultant of the motion of arrow A, the retaining pin 10 is caused to also move toward the anvil. In fact, it has been observed that it is more desirable to have the retaining pin 10 initially be inserted into the anvil 7. Then, the cartridge 9 acts as a following mechanism, so that it is guided by the retaining pin 10.

The operation of the gap-setting screw 30 in cooperation with cartridge 9 will now be explained. As noticed in FIG. 6, the gap-setting screw 30 is connected at pins 30a, 30b to a pair of side panels 31, 32, which are independent of the four-bar linkage which forms the fast closure mechanism. These side panels 31, 32 are adherently affixed to the anvil 7. Thus, motion of the screw (as indicated by the arrow B acting on knob 36 in FIG. 3) causes the side panels 31, 32 to move the anvil 7 toward cartridge 9. This in turn reduces the gap between slider block 20 and the anvil 7. In this manner, the anvil 7 is caused to move backward (relative to the cartridge 9), as indicated by the arrow B', within an acceptable gap G away from the cartridge 9.

Figure 3:
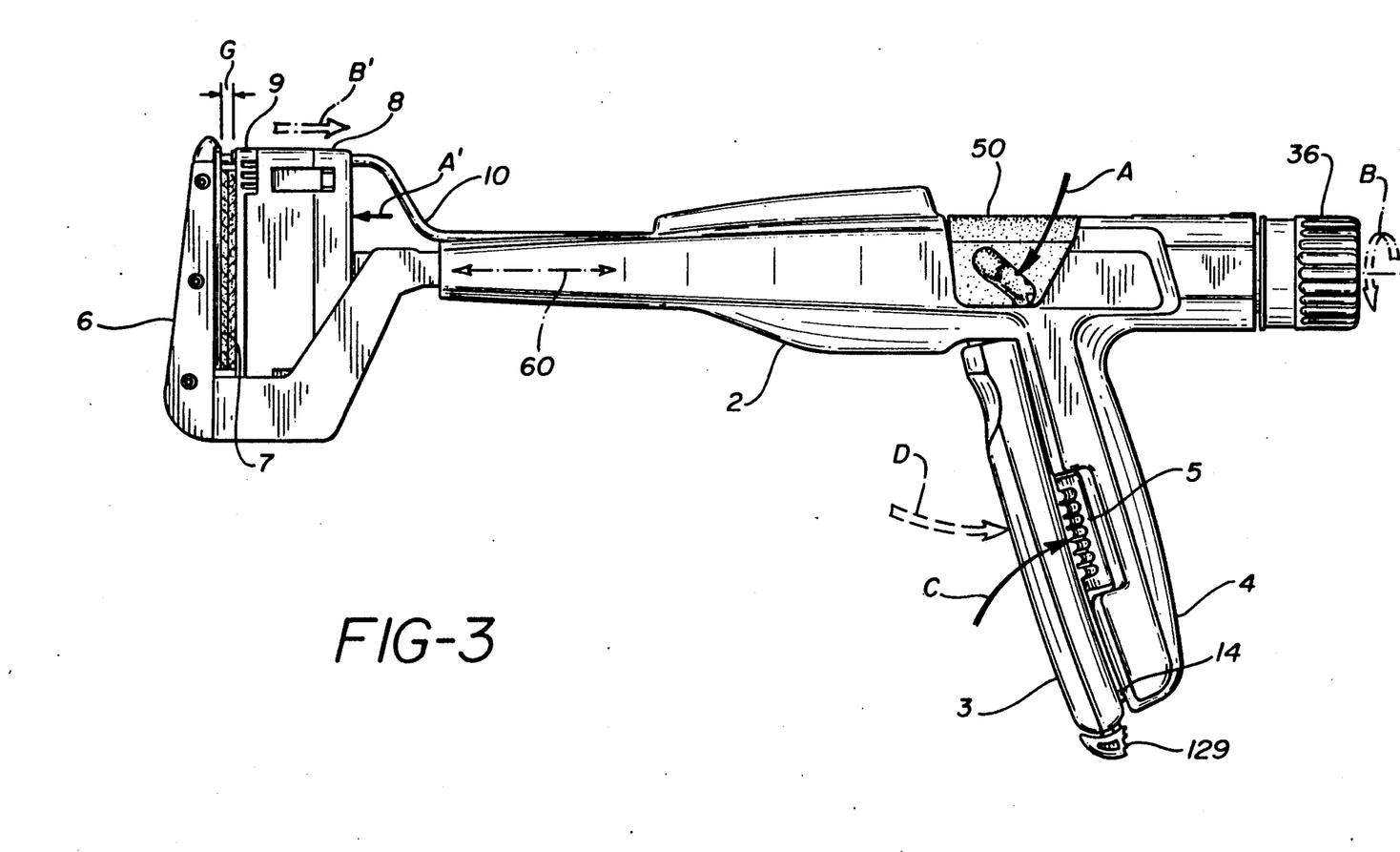
FIG. 3 is a side view of the stapler showing the necessary steps needed to be taken in order to move the stapler to a closed and locked position.

It is furthermore to be noticed that the trigger assembly cooperates with the gap-setting assembly in order to provide a number of safety mechanisms for the stapler. Thus, when the gap assembly moves as indicated in FIGS. 3 and 6, it is only upon the proper approximation of the gap G that the safety interlock 94 on trigger lever 39, will have enough clearance to allow release of safety 5. The gap must be appropriately set before the safety interlock 94 is adequately clear of a post (not shown) placed on right side panel 32. In this fashion, there is applied a redundant safety mechanism. That is, in addition to the more typical safety accomplished by trigger safety 5, safety interlock 94 serves as a locking mechanism for trigger safety 5.

Furthermore, as seen in FIG. 4, connecting arm 51 must also be rotated into place, so that node 101 on trigger 3 can operate within cut-out portion 102 on connecting arm 51. Without this step being performed, node 101 will not have enough clearance to give safety interlock 94 and trigger lever 39 freedom of motion. In addition, when connecting arm 51 is rotated into place, top 37a of trigger lever 39 will contact push portion 37b on connecting arm 51. This, in turn, allows forward face 37c of connecting arm to contact transverse plate 47 of slider block 20 connected to driver rod 17. Only then will there be allowed operation of the driving mechanism.

Trigger safety 5 operation is indicated at arrow C on FIG. 3 as well as can be seen in FIGS. 3 and 4. One must affirmatively move safety 5 so that it can be rotated into place along the handle 4 of the mechanism.

Thus, the stapler is only ready to be fired as shown in phantom arrow D in FIG. 3 after this double safety mechanism has been accomplished. That is, the instrument 10 must be closed as at arrow A and the gap must be appropriately set as seen by arrow B and understood from FIGS. 3, 4, 5 and 6. Then, the safety 5 can be released as seen arrow C, and more better understood in FIGS. 3 and 4. After the trigger 3 is fired as seen in arrow D in phantom in FIG. 3, the trigger 3 is held to the rearward handle by catch 143 contained on the rearward handle which interlocks with detent slot 128 on the trigger 3. Only upon relaxation of the release 129 on the trigger will the trigger 3 be able to move away from the handle 4. Thus, refiring is impossible unless affirmatively overcome by the user. This can be important when a refiring is attempted inadvertently by the user.

Therefore, in operation it is seen that this stapler accomplishes many various inter related and useful functions. First, the tissue is placed between the loaded cartridge 9 and the anvil 7. Then, the fast closure mechanism is actuated by placing a downward and rotational force on lever 50 as arrow A on FIG. 3. This force causes crank 52 and connecting arm 51 to rotate into a parallel position with the axis 60 of the shaft of the stapler body 2. During this, the cam 83 and camming surfaces 80 located in FIG. 6 interreact so that the retaining pin 10 is caused to be inserted into the anvil 7. Thereafter, the cartridge 9 is approximated near the anvil 7, as seen by arrow A' in FIG. 3.

When it is determined that the retaining pin 10 is properly emplaced at the anvil 7, and the cartridge 9 is near enough to the anvil 7, the gap G is set by adjusting gap setting screw 36, as shown by rotational arrow B on FIG. 3. This rotation causes the cartridge 9 and driver 15 assembly to be properly approximated by having anvil 7 moved toward cartridge 9. This relative motion is seen by arrow B' in FIG. 3. Also, this rotation of the screw 36 causes the trigger 3 assembly to be properly put in place, by motion of side panels 31, 32 toward the handle 4, so that operation of the trigger 3 in conjunction with handle 4 now becomes possible.

Upon appropriate approximation of the cartridge 9 and anvil 7 with the tissue contained therebetween, the trigger safety 5 is released as shown by arrow C on FIG. 3. Once the trigger safety 5 is released, the stapler is ready for firing. It is only ready in that the redundant safety systems have been overcome and the tissue is properly approximated to the anvil 7 and cartridge 9.

Thereafter, the trigger 3 is fired so that the motion of the trigger is accomplished as in phantom arrow D in FIG. 3, and the trigger is made to rotate rearward toward handle 4 of the instrument. Trigger 3 rotates so that the drivers 15 are actuated so that staples pierce the tissue and are clinched at the anvil 7. Stapling is accomplished in a quick, efficient and safe manner.

It will be understood that the surgical stapling instrument of this invention has been described in terms of the Figures as they appear in the drawings. Use of such terms as "forward", "rearward", "top", "bottom", and the like, both in the specification or in the claims, is simply for clarity of description and explanation. One skilled in the art will understand that the instrument may assume any appropriate position during use. Furthermore, it is to be understood that the invention is to be taken from the attached claims and their equivalents.

What is claimed is:

1. A surgical stapler comprising a shaft containing firing means and with a cartridge of staples and an anvil surface for forming said staples, and a fast closure mechanism to bring said cartridge into proximal contact with said anvil surface to fire said staples using said firing means, wherein said fast closure mechanism is a slider-crank four bar linkage; and
    wherein said slider is a block attached to said cartridge constrained in the shaft of said stapler such that said block with said cartridge attached may move linearly toward or away from said anvil; and
    wherein said crank portion of said four-bar linkage has a crank pivotable about said shaft and a connecting arm, and is attached to said slider block by means of a pin held within said slider block; and
    wherein said connecting arm contains a cam mechanism cooperating with a link containing a camming surface, said link operating a placement pin moving parallel to said slider block said placement pin movable relative to said cartridge to become emplaced in said anvil.

2. The stapler of claim 1 wherein said cam surface on said link is two-sided so that it cooperates with said cam on said connecting arm when moving in either a proximal or a distal direction from said anvil surface.

3. The stapler of claim 2 wherein said link operates as a crank mechanism with respect to said placement pin, and said placement pin operates as a slider, such that said crank, said link and said placement pin operate as a second distinct four-bar linkage.

4. The stapler of claim 3 wherein said pair of four-bar linkages cooperate to bring said placement pin and said cartridge in proximity to said anvil.

5. The stapler of claim 4 further comprising a gap-setting screw cooperating with said anvil in order to place said anvil at a desirable distance away from said proximally located cartridge.

6. The stapler of claim 5 containing an interlocking mechanism operable in cooperation with said gap-setting screw and said firing means in order to prevent operation of said firing means until said screw has placed said cartridge within a predetermined distance from said anvil.

7. The stapler of claim 1 wherein said sliding block is connected to said shaft by spring means, such that said spring means tend to keep said cartridge spaced apart from said anvil.

8. The stapler of claim 1 further comprising a slot on said connecting arm cooperating with aid pin to insure motion of said slider block along said shaft.

9. A surgical stapler comprising a shaft having a longitudinal axis, firing means, a cartridge of staples, an anvil surface for forming said staples, and a placement pin for enclosing tissue between said anvil and said cartridge, said placement pin movable relative to said cartridge, wherein said placement pin and said cartridge move parallel to each other along said shaft longitudinal axis, and said parallel motion of said cartridge and placement pin are controlled by a pair of separate but cooperating four-bar linkages.

10. The stapler of claim 9 wherein said first linkage is a slider-crank mechanism comprising a slider block attached to said cartridge and constrained in said shaft such that said cartridge may slide linearly along said shaft toward or away from said anvil.

11. The stapler of claim 10 wherein said first linkage further comprises a crank and connecting arm and a pin on said slider block operable on a slot contained within said connecting arm.

12. The stapler of claim 9 wherein said second four-bar linkage contains a link with a camming surface, said link in sliding contact with said placement pin, and said camming surface in contact with a cam member on a connecting arm, wherein said camming surface is two-sided such that it contacts said cam independent of the direction of motion of said placement pin.

13. The stapler of claim 11 wherein said second four-bar linkage contains a link with a camming surface, said link in sliding contact with said placement pin, and said camming surface in contact with a cam member on a connecting arm, wherein said camming surface is two-sided such that it contacts said cam independent of the direction of motion of said placement pin.

14. The stapler of claim 13 wherein said placement pin and said cartridge are brought into proximity of said anvil when said crank and said connecting arm are parallel to said shaft.

15. The stapler of claim 14 further comprising a gap-setting screw cooperating with said anvil in order to place said anvil at a desirable distance away from said proximally located cartridge.

16. The stapler of claim 15 containing an interlocking mechanism operable in cooperation with said gap-setting screw and said firing means in order to prevent operation of said firing means until said screw has placed said cartridge within a predetermined distance from said anvil.

17. The stapler of claim 9 wherein said trigger is prevented from firing by an interlocking mechanism actuable dependent upon the operation of said four-bar linkages to bring said cartridge into proximity with said anvil surface.

18. The stapler of claim 10 wherein said sliding block is connected to said shaft by spring means, such that said spring means tend to keep said cartridge spaced apart from said anvil.

* * * * *